(12) United States Patent (10) Patent No.: US 11,672,994 B2
Neils et al. (45) Date of Patent: Jun. 13, 2023

(54) ELECTRICAL STIMULATION DEVICE WITH MINIMALLY INVASIVE DELIVERY

(71) Applicant: Medtronic, Inc., Minneapolis, MN (US)

(72) Inventors: Thomas F. Neils, Orono, MN (US); Andrew J. Cleland, St. Paul, MN (US); Phillip C. Falkner, Minneapolis, MN (US); Kyle Dahlstrom, Eden Prairie, MN (US); Jonathan C. Sell, Eagan, MN (US); Jerel K. Mueller, St. Paul, MN (US); Forrest C.M. Pape, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 100 days.

(21) Appl. No.: 16/857,747

(22) Filed: Apr. 24, 2020

(65) Prior Publication Data

US 2021/0330985 A1 Oct. 28, 2021

(51) Int. Cl.
*A61N 1/37* (2006.01)
*A61N 1/375* (2006.01)
(Continued)

(52) U.S. Cl.
CPC ........ *A61N 1/3758* (2013.01); *A61B 17/3468* (2013.01); *A61N 1/0551* (2013.01); *A61N 1/36128* (2013.01); *A61N 1/3787* (2013.01); *A61N 1/37229* (2013.01); *A61N 1/37518* (2017.08); *A61B 17/00234* (2013.01)

(58) Field of Classification Search
CPC .............. A61N 1/37518; A61N 1/0551; A61N 1/36128; A61N 1/37229; A61N 1/3787
See application file for complete search history.

(56) References Cited

U.S. PATENT DOCUMENTS 6,167,312 A * 12/2000 Goedeke .............. H04B 7/0602
607/32
8,634,919 B1 * 1/2014 Hou ........................ A61N 1/368
607/36

(Continued)

FOREIGN PATENT DOCUMENTS

EP 3311880 A1 4/2018
WO 2019191423 A1 10/2019

OTHER PUBLICATIONS

International Search Report and Written Opinion of International Application No. PCT/US2021/028185, dated Aug. 25, 2021, 11 pp.

(Continued)

*Primary Examiner* — Eric D. Bertram
(74) *Attorney, Agent, or Firm* — Shumaker & Sieffert, P.A.

(57) ABSTRACT

The disclosure describes example devices, systems, and techniques for delivering electrical stimulation to a patient. In some examples, an IMD includes a housing having a main portion and projection extending from the main portion. The projection of the housing may carry an electrode. Stimulation circuitry may be disposed within the main portion of the housing where the stimulation circuitry may generate electrical stimulation deliverable via the electrode. Processing circuitry may be disposed within the main portion of the housing where the processing circuitry may control the stimulation circuitry to generate the electrical stimulation.

21 Claims, 13 Drawing Sheets

(51) Int. Cl.
  *A61B 17/34*   (2006.01)
  *A61N 1/05*    (2006.01)
  *A61N 1/36*    (2006.01)
  *A61N 1/372*   (2006.01)
  *A61N 1/378*   (2006.01)
  *A61B 17/00*   (2006.01)

(56) References Cited

U.S. PATENT DOCUMENTS

| | | | | |
|---|---|---|---|---|
| 9,821,159 | B2* | 11/2017 | Ackermann | A61N 1/36046 |
| 10,463,295 | B2 | 11/2019 | Zhou | |
| 2002/0055761 | A1* | 5/2002 | Mann | A61N 1/36071 |
| | | | | 607/41 |
| 2003/0135246 | A1* | 7/2003 | Mass | A61N 1/08 |
| | | | | 607/60 |
| 2007/0027496 | A1* | 2/2007 | Pam | A61N 1/3601 |
| | | | | 607/42 |
| 2007/0255339 | A1* | 11/2007 | Torgerson | A61N 1/0529 |
| | | | | 607/45 |
| 2009/0326608 | A1* | 12/2009 | Huynh | A61N 1/37247 |
| | | | | 607/59 |
| 2010/0274313 | A1* | 10/2010 | Boling | A61N 1/37217 |
| | | | | 607/116 |
| 2014/0107723 | A1* | 4/2014 | Hou | A61N 1/3756 |
| | | | | 607/9 |
| 2014/0275837 | A1* | 9/2014 | Katra | A61B 5/4818 |
| | | | | 600/377 |
| 2017/0312521 | A1* | 11/2017 | Franke | A61N 1/0546 |
| 2019/0001137 | A1* | 1/2019 | Torgerson | A61N 1/37241 |

OTHER PUBLICATIONS

International Preliminary Report on Patentability from International Application No. PCT/US2021/028185 dated Nov. 3, 2022, 6 pp.

* cited by examiner

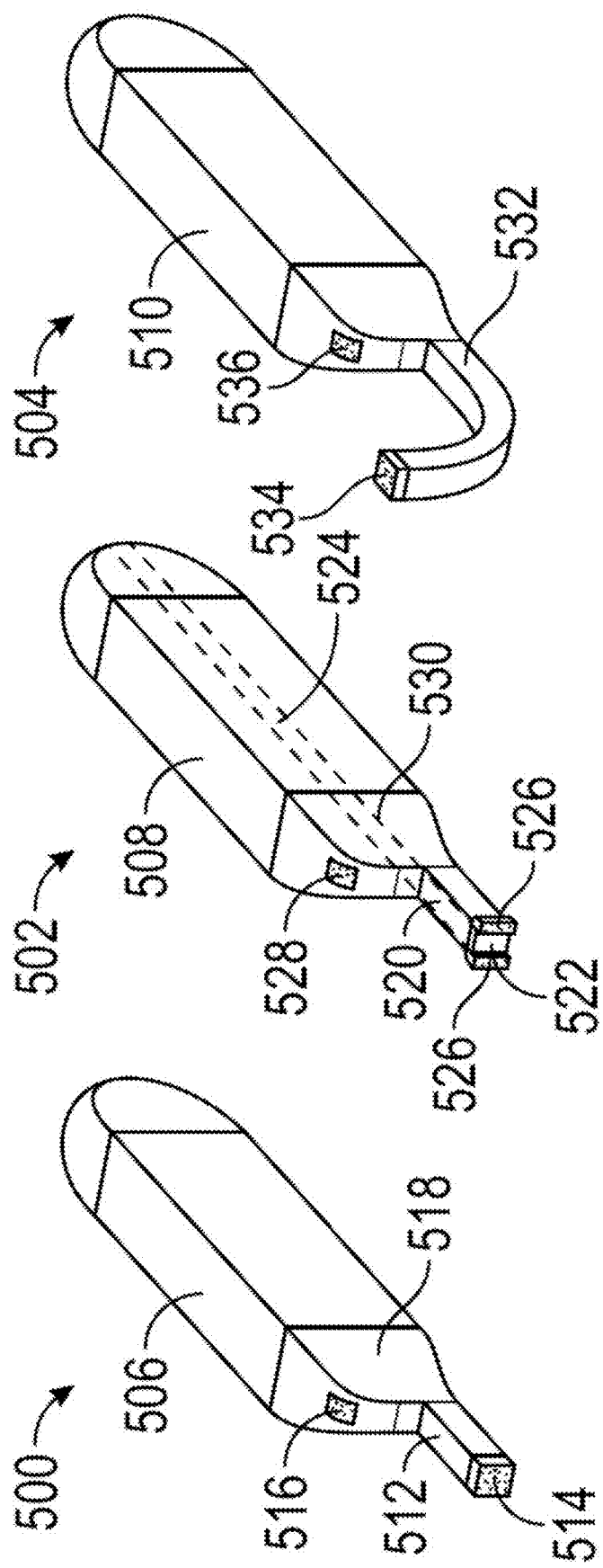

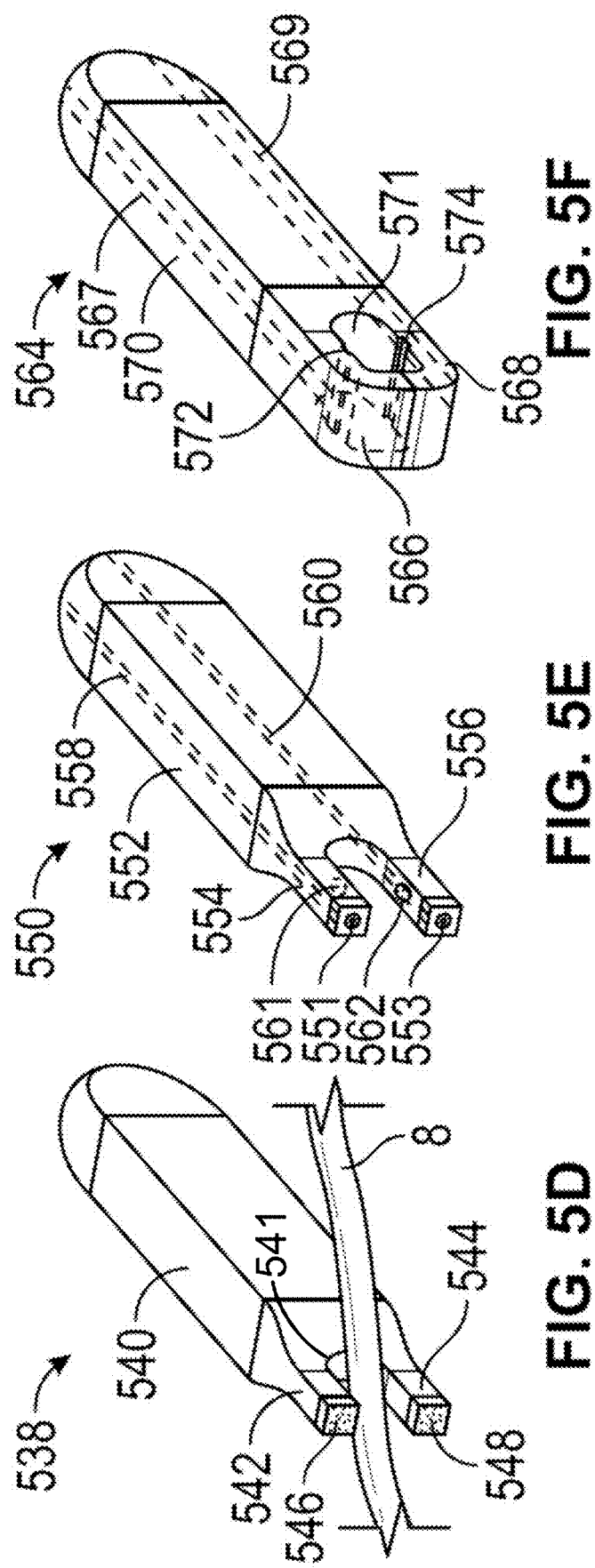

ELECTRICAL STIMULATION DEVICE WITH MINIMALLY INVASIVE DELIVERY

TECHNICAL FIELD

The disclosure relates generally to medical devices and, more particularly, medical device systems configured to deliver electrical stimulation.

BACKGROUND

Medical devices may be external or implanted and may deliver electrical stimulation therapy to patients to various tissue sites to treat a variety of symptoms or conditions such as chronic pain. A medical device may deliver electrical stimulation therapy via one or more leads that include electrodes located proximate to target locations associated with the brain, heart, spinal cord, peripheral nerves, muscle, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve and peripheral nervefield stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, a pulse frequency, inter-pulse interval, and cycling of therapy as stimulation parameters. A set of parameters, such as a set including electrode combination, electrode polarity, amplitude, pulse width, pulse rate, interpulse interval, and cycling may be referred to as a program in the sense that they define the electrical stimulation therapy to be delivered to the patient.

SUMMARY

In general, the disclosure is directed to devices, systems, and techniques for stimulating nerves (e.g., a peripheral nerve) at varying tissue depths with an implantable medical device (IMD) implantable via minimally invasive delivery. An IMD described herein may have a relatively small cross-sectional profile allowing for passage through tissue and implantation close to one or more target nerves for stimulation. The IMD may include stimulation electrodes disposed on one end of the IMD that may be disposed close to the target one or more nerves. One or more of the electrodes may be disposed on a respective projection that extends from the main housing of the IMD in order to position the electrodes close to the target one or more nerves. In some examples, the one or more projections may be curved to capture the target one or more nerves. In some examples, the IMD may have a small cross-sectional profile and thus configured to be placed subcutaneously in order to provide electrical stimulation to peripheral nerves.

The IMD may have an onboard power source or be externally powered. For example, the IMD may include a rechargeable power source that can be recharged wirelessly from an external recharging device. A main portion of the housing of the IMD may include a rechargeable power supply and a secondary coil configured to receive power wirelessly from an external charging device. In some examples, the IMD may have a coil shaped housing a recharging coil (e.g., a secondary coil) configured to receive power via inductive charging from an external device. Further, the coil shaped may be configured as a tether that facilitates removal and/or replacement of the IMD. The electrodes and/or secondary coil of the IMD enable recharging when the IMD is implanted at various angles in respect to the patient's skin.

In some examples, this disclosure describes an IMD including a housing including a main portion and projection extending from the main portion. The IMD also includes an electrode carried by the projection of the housing and stimulation circuitry disposed within the main portion of the housing, wherein the stimulation circuitry is configured to generate electrical stimulation deliverable via the electrode. The IMD also includes processing circuitry disposed within the main portion of the housing, wherein the processing circuitry is configured to control the stimulation circuitry to generate the electrical stimulation.

In some examples, this disclosure describes a method for controlling, by processing circuitry disposed within a housing of an IMD, stimulation circuitry of the IMD to generate electrical stimulation. The housing includes a main portion and a projection extending from the main portion, and the projection of the housing carries an electrode. The stimulation circuitry and the processing circuitry are disposed within the main portion of the housing. The example method also includes delivering, via the electrode carried by the projection, the electrical stimulation to a target nerve.

In some examples, this disclosure describes an IMD including a housing including a main portion and a first projection extending from the main portion. The IMD also includes a second projection extending from the main portion, wherein the first projection and the second projection are configured to be disposed on opposing sides of a nerve. The IMD includes a first electrode carried by the first projection of the housing and a second electrode carried by the second projection of the housing. The IMD also includes stimulation circuitry disposed within the main portion of the housing, wherein the stimulation circuitry is configured to generate electrical stimulation deliverable via the first or second electrode. The IMD also includes processing circuitry disposed within the main portion of the housing, wherein the processing circuitry is configured to control the stimulation circuitry to generate the electrical stimulation. The IMD also includes charging circuitry disposed within the main portion of the housing, wherein the charging circuitry is configured to control current from a secondary coil to a rechargeable power source of the implantable medical device.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIGS. 5A, 5B, 5C 5D, 5E, 5F, 5G, 5H, 5I, and 5J are conceptual drawings illustrating additional example IMDs that may be similar to the IMD of FIGS. 1-3, but which may include one or more additional features, in accordance with one or more techniques described herein.

Like reference characters denote like elements throughout the description and figures.

DETAILED DESCRIPTION

Figure 1:
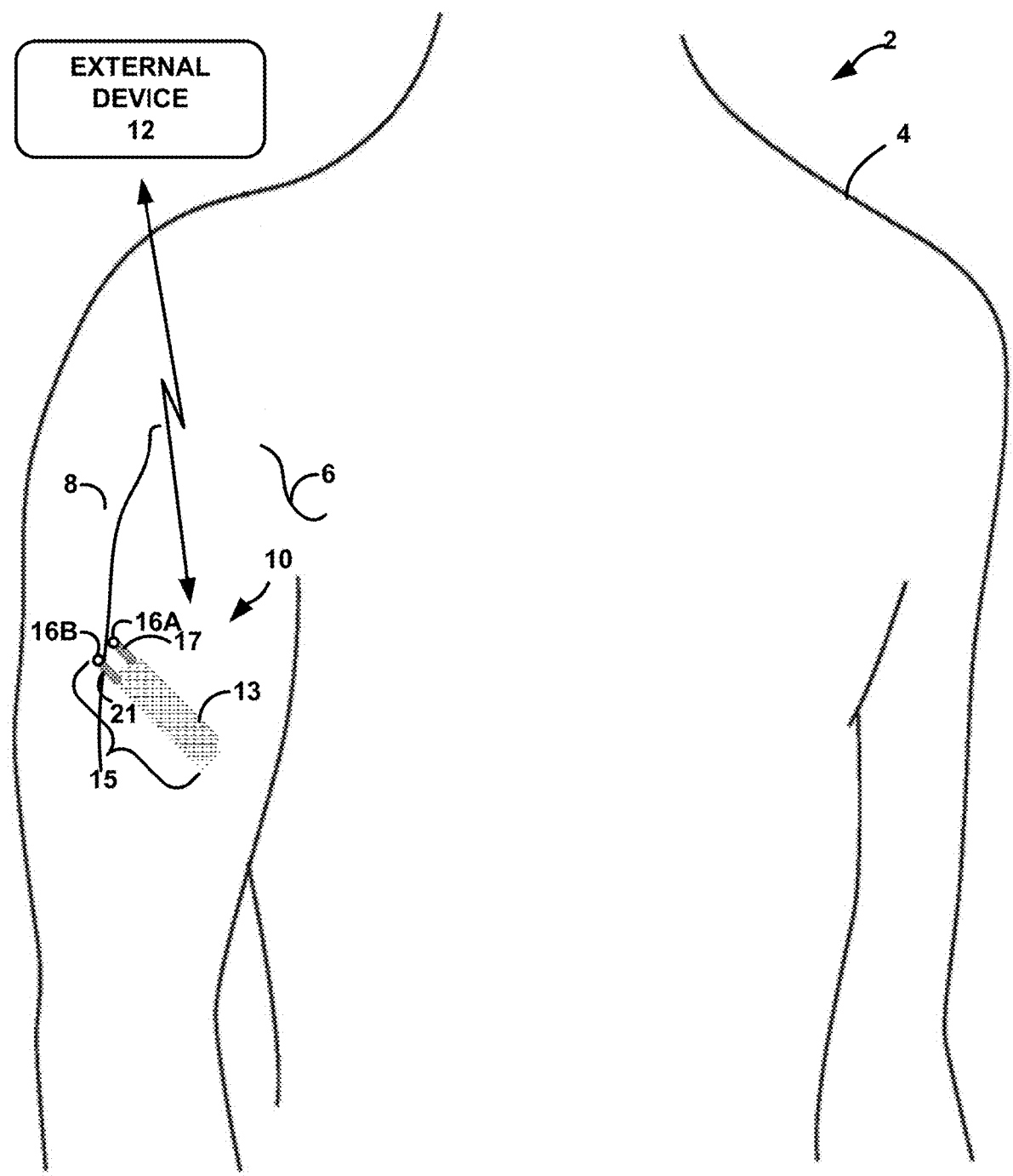
FIG. 1 is a conceptual drawing illustrating an example of a medical device system in conjunction with a patient, in accordance with one or more techniques described herein.

In general, the disclosure is directed to devices, systems, and techniques for stimulating one or more nerves (e.g., one or more peripheral nerves) with an IMD implanted via minimally invasive delivery. An implantable lead may be implanted adjacent a target nerve in order for an IMD to deliver electrical stimulation the that target nerve to reduce or eliminate pain sensation. Stimulating nerves in the periphery of a patient is difficult due to the depth and locations of target nerves within a patient (e.g., the wrist and forearm). For example, an implantable lead is relatively large in relation to peripheral nerve locations which can cause challenges for tunneling the lead to the target nerve. In addition, the IMD is placed in another location, commonly the torso, which requires the lead to be tunneled a distance under the skin from the nerve to the IMD location. The lead is thus subjected to repetitive bending forces while implanted. Further, the implantable lead may only position electrodes along one side of the nerve. This position of electrodes may require a relatively large stimulus amplitude in order to produce an electrical field large enough to cause the desired effect at the target nerve. Moreover, implantation of multiple items, such as the IMD and the lead, requires extended time for implant procedure planning and execution for the clinician and patient.

As described herein, an IMD may have a housing that carries multiple electrodes to provide electrical stimulation to one or more target nerves (e.g., one or more peripheral nerves or other nerves). For example, the multiple electrode configuration may include one or more electrodes on respective projections from the housing. The one or more projections may be configured to position the electrodes on either side of the target nerve. The projections may be firm, semi-firm, or flexible. The electrodes of the IMD placed on either side of the target nerve may enable the IMD to deliver efficacious stimulation with less power than a lead implanted along one side of the nerve. This IMD may also be implanted near the target nerve via a minimally invasive approach at a tissue depth appropriate for stimulating the nerve.

For example, the housing of the IMD may have a small cross-sectional profile that facilitate insertion through tissue, and the electrodes extending from the housing on one or more respective projections may enable the IMD to be implanted substantially parallel to a peripheral nerve. In this position, the IMD may be implanted at a position shallow from the patient's skin (e.g., wrist/forearm targets, subcutaneously). Additionally, the low cross-sectional profile housing of the IMD may enable the IMD to be implanted via a minimally invasive approach for deep anatomical targets (e.g., an ilioinguinal nerve or a peripheral nerve within a deeper depth of tissue). As described in more detail below, the electrode configuration on the housing of the IMD may enable the IMD to be implanted as different angles with respect to the target nerve. In addition, instead of having to implant a medical lead close to the nerve and another device at another location, the IMD housing may include the electrodes that are configured to be implanted close to the nerve. This IMD may be injectable in a single step, which can avoid tunneling a flexible lead between the target nerve and the pocket at which another implant is to be implanted.

The IMD housing may also include a power supply. In some examples, the power supply may be rechargeable via a secondary coil. The electrodes of the IMD enable the IMD to be implanted at different angles with respect to the target nerve to position the secondary coil in an appropriate distance from the skin to receive rechargeable power from a primary coil of an external charging device. In some examples, a recharging system having an appendage (e.g., with a coiled shape) extending from the IMD housing may extend toward the surface of the skin. This may enable the IMD to receive recharge power or external power from an external device for stimulation therapy. Further, with the appendage extending toward the skin may enable positioning of the secondary coil within tissue while the IMD housing, and carried electrodes, can be implanted at an appropriate position and angle with respect to the target nerve for therapy. Therefore, the appendage that includes the secondary coil may enable RF coupling with an external charging device and location of the IMD at varying anatomical depths.

FIG. 1 illustrates the environment of an example medical device system 2 in conjunction with a patient 4, in accordance with one or more techniques of this disclosure. The example techniques may be used with an IMD 10, which may be in communication with an external device 12. In some examples, IMD 10 may be implanted in adipose tissue just underneath the skin 6 (e.g., subcutaneously) in contact with, adjacent to or near one or more nerves 8 of patient 4. In some examples, IMD 10 may have a low-profile form with a volume of 3 cubic centimeters ($cm^3$) or less, 1.0 $cm^3$ or less, or any volume therebetween. In some examples, IMD 10 may have a length of 50 mm or less, 40 mm or less or any distance in between, a width of 8 mm or less, 7 mm or less, or any distance in between, and a depth of 5 mm or less, 4 mm or less, or any distance in between. In this manner, the cross-sectional profile (e.g., the width by the depth) may be less than 40 square mm. External device 12 may be a computing device configured for use in settings such as a home, clinic, or hospital, and may further be configured to communicate with IMD 10 via wireless telemetry including updating of parameters including stimulation parameters. In one example, external device 12 may be coupled to a remote patient monitoring system, such as Carelink®, available from Medtronic plc, of Dublin, Ireland. External device 12 may, in some examples, include or be a programmer, an external charging device, an external monitor, and/or or a consumer device such as a smart phone or tablet.

IMD 10 may include a housing 15 comprising a main portion 13 and projection 17 extending from main portion 13. Stimulation circuitry (not illustrated in FIG. 1) may be disposed within main portion 13 of housing 15. The stimulation circuitry may generate electrical stimulation deliverable via electrode 16A. Processing circuitry (not illustrated in FIG. 1) may be disposed within main portion 13 of housing 15. The processing circuitry may control the stimulation circuitry to generate the electrical stimulation. Charging circuitry (not illustrated in FIG. 1) may be disposed within main portion 13 of housing 15.

IMD 10 may include a second electrode 16B carried by a second projection 22 of housing 15. The stimulation circuitry may generate electrical stimulation deliverable to first electrode 16A and/or second electrode 16B. In an example, projection 17 and projection 21 may extend from main portion 13 in approximately the same direction. In another example, projection 17 and projection 21 extend straight out from main portion 13 of housing 15. In another example, projection 17 may have a curved distal portion curved towards second projection 21 (illustrated in FIG. 5F).

IMD 10 provides for a low-profile housing 15 which may be implanted close to the surface of skin 6 with electrode 16A and/or 16B close to a target nerve, such as nerve 8. Housing 15 may carry electrodes 16A and/or 16B on projections 17 and 21, respectively. Medical device system 2 may provide a minimally invasive approach to stimulating nerve 8 at varying depths under skin 6. Electrode(s) 16A and/or 16B located on housing 15 may simplify an implantation procedure for IMD 10, compared with an implantable device with electrode leads, as electrodes 16A and/or 16B extend from low-profile housing 15, which may be implanted subcutaneously with electrodes 16A and/or 16B close to nerve 8 in a minimally invasive procedure. As shown in FIG. 1, electrodes 16A and 16B may be located on either side on target nerve 8. Projections 17 and 21 enable for electrodes 16A and 16B to be placed close to and on either side on target nerve 8.

Medical device system 2 may stimulate varying nerve locations. For example, IMD 10 may be implantable in the same plane as a nerve, such as the dorsal branch nerve, and shallow within the tissue (e.g., wrist/forearm neve targets). Conversely, IMD 10 may for minimally invasive implantation for deep anatomical targets (e.g., illoginual nerve). In examples of the disclosure, nerve 8 may be stimulated to reduce or eliminate pain sensation. Stimulating nerve 8 may be performed with low energy when electrode(s) 16A and/or 16B are in close proximity to nerve 8. IMD 10 may have a power source (not illustrated in FIG. 1) with one or more electrode configurations to stimulate nerve 8 with minimal energy. Minimal energy is necessary to provide adequate simulation as electrodes 16A and/or 16B are located on either side or generally opposing sides of target nerve 8 instead of only along one side of target nerve 8.

IMD 10, which may be similar in size to the LINQ™ device manufactured by Medtronic, Inc. in some examples, may have a small energy requirement which may be supported by an onboard power source or by external device 12. Electrodes 16A and 16B may be located at near or on nerve 8, and the close proximity allows for very low energy to stimulate nerve 8. Stimulation parameters may be less than 2 mA at less than 100 Hz with a 1 millisecond pulse width. The therapy is cycled on and off. Higher frequencies and lower amplitudes have been shown to provide pain relief. It would be possible to deliver 10 kHz frequencies with external power. In some examples, a 500 kHz energy at a low amplitude may be delivered over a shorter time duration using external power Thus, with a low power requirement a primary (e.g., non-rechargeable) power source of IMD 10 may last between 1 to 5 years in some examples before IMD 10 may need to be replaced. The low power requirement may also enable a rechargeable power supply to last longer between charging sessions due to the lower stimulation signal power requirements when compared to a leaded system.

In an example of the disclosure, external device 12 may operate as a charging device and provide inductive charging to IMD 10 through skin 6. If IMD 10 is implanted shallow under skin 6, a primary coil (not shown in FIG. 1) of external device 12 may inductively couple with a secondary coil (not shown in FIG. 1) onboard IMD 10. In this manner, the magnetic field generated by the primary coil induces current in the secondary coil that recharging circuitry uses to recharge the power source onboard IMD 10. When IMD 10 is implanted in a shallow manner (e.g., where nerve 8 is close to the surface of skin 6), IMD 10 can be placed horizontally or substantially horizontal with respect to skin 6 and still be close enough to IMD 10 to inductively couple with external device 12. If target nerve 8 is deeper within the adipose underneath skin 6, the implanting clinician may implant IMD 10 in a vertical or substantially vertical orientation with respect to the skin so the secondary coil of IMD 10 is closer to skin 6 and thus closer to external device 12 during an inductive recharging session.

External device 12 may be used to program commands or operating parameters into IMD 10 for controlling electrical stimulation and/or other device functions (e.g., when configured as a programmer for IMD 10). In some examples, external device 12 may be used to interrogate IMD 10 to retrieve data, including device operational data as well as physiological data accumulated in IMD memory. Such interrogation may occur automatically according to a schedule or may occur in response to a remote or local user command. Programmers, external monitors, and consumer devices are examples of external device 12 that may be used to interrogate IMD 10. Examples of communication techniques used by IMD 10 and external device 12 include radiofrequency (RF) telemetry, which may be an RF link established via Bluetooth®, Near Field Communication (NFC), Wi-Fi, or medical implant communication service (MICS). In some examples, external device 12 may include a user interface configured to allow a clinician to remotely interact with IMD 10.

Figure 2:
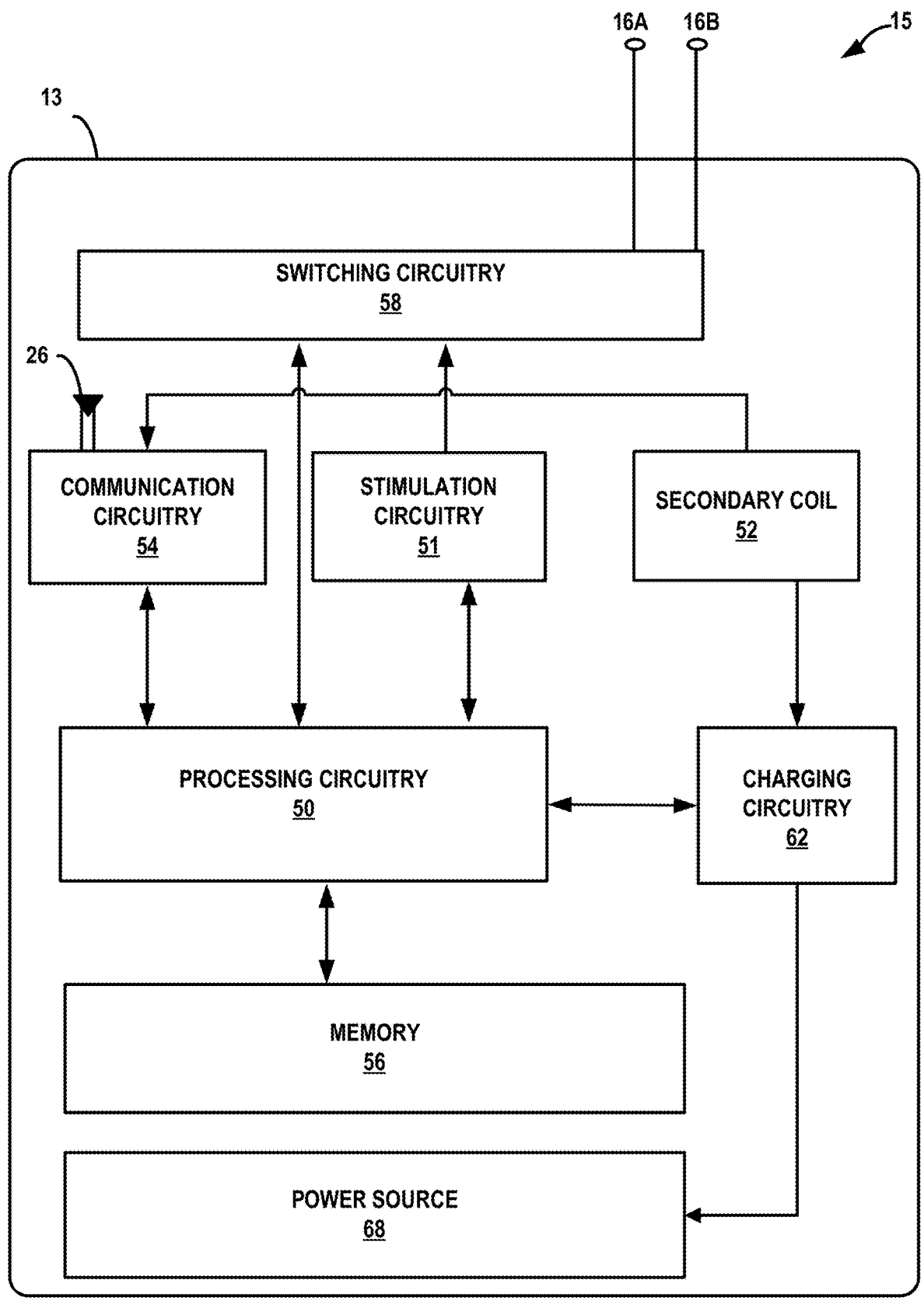
FIG. 2 is a functional block diagram illustrating an example configuration of the IMD of FIG. 1 in accordance with one or more techniques described herein.
Figure 3:
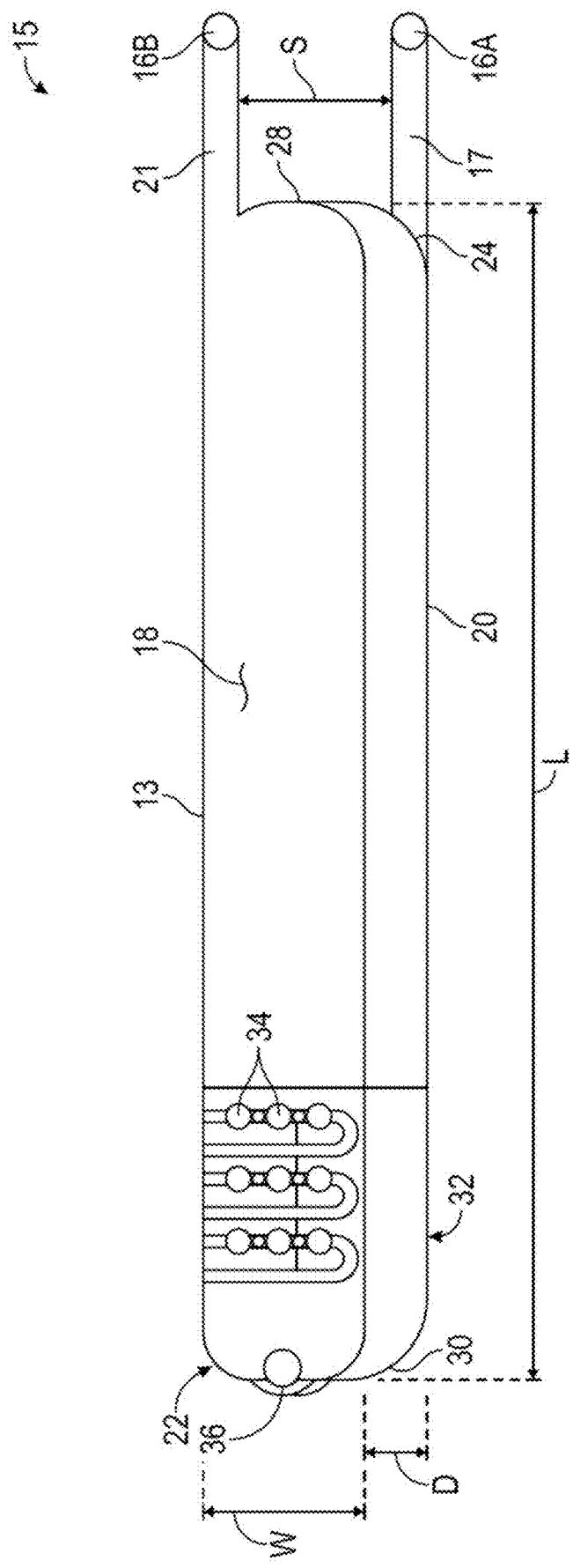
FIG. 3 is a conceptual drawing illustrating an example configuration of the IMD of the medical device system of FIGS. 1 & 2, in accordance with one or more techniques described herein.
Figure 4:
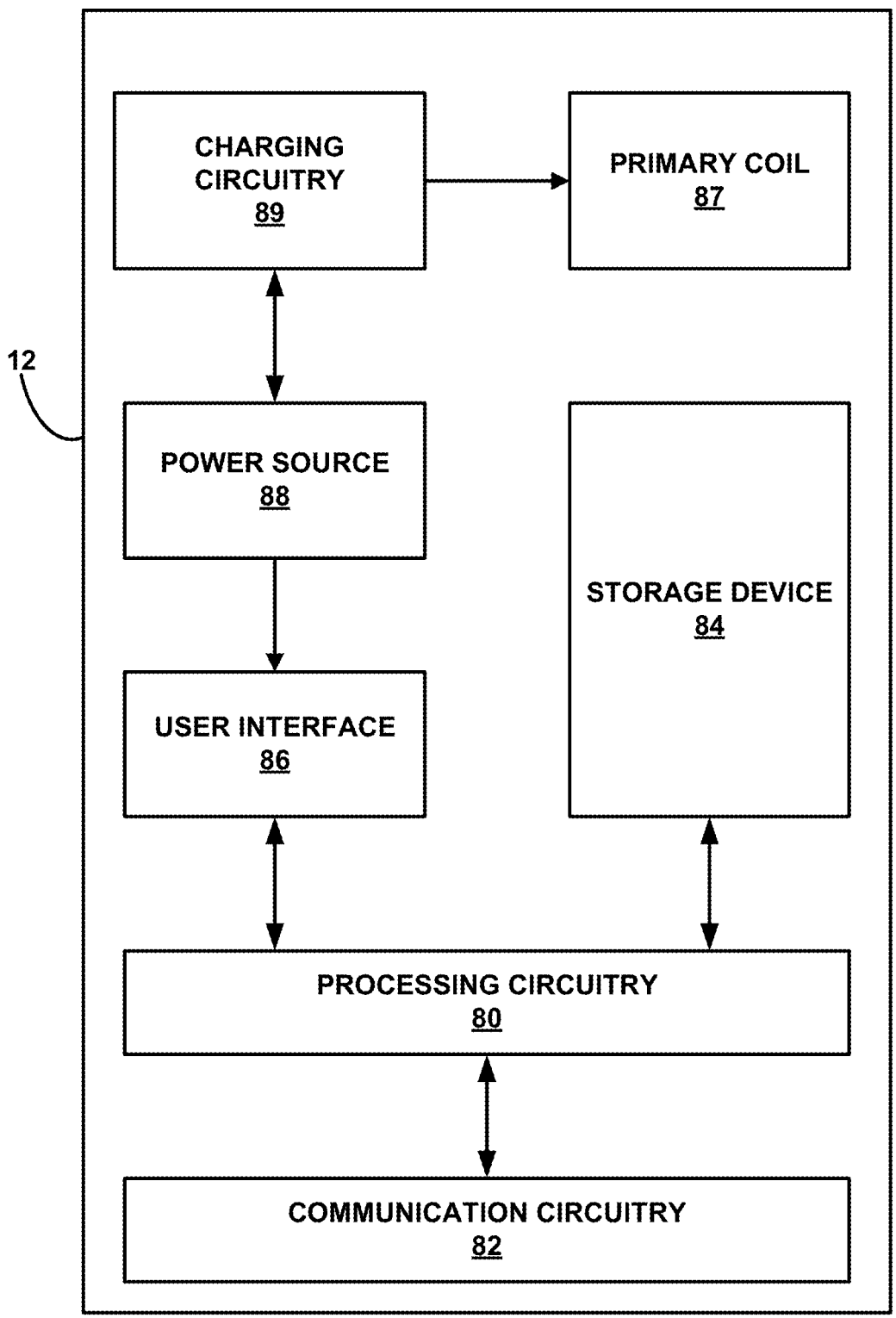
FIG. 4 is a block diagram illustrating an example configuration of components of the external device of FIG. 1, in accordance with one or more techniques of this disclosure.

FIGS. 2-4 illustrate various aspects and example arrangements of IMD 10 of FIG. 1. FIG. 2 is a block diagram illustrating an example configuration of components within IMD 10. FIG. 3 conceptually illustrates an example perspective view of IMD 10. FIG. 4 is a block diagram illustrating an example configuration of components of the external device of FIG. 1, in accordance with one or more techniques of this disclosure. It should be understood that any of the examples of IMD 10 described below with respect to FIGS. 1-3 may be used to implement the techniques described herein.

FIG. 2 is a functional block diagram illustrating an example configuration of IMD 10 of FIG. 1, in accordance with one or more techniques described herein. In the illustrated example, IMD 10 includes electrodes 16A & 16B, antenna 26, processing circuitry 50, stimulation circuitry 51, secondary coil 52, communication circuitry 54, memory 56, switching circuitry 58, charging circuitry 62 and power source 68. In some examples, memory 56 includes computer-readable instructions that, when executed by processing circuitry 50, cause IMD 10 and processing circuitry 50 to perform various functions attributed to IMD 10 and processing circuitry 50 herein. Memory 56 may include any volatile, non-volatile, magnetic, optical, or electrical media, such as a random access memory (RAM), read-only memory (ROM), non-volatile RAM (NVRAM), electrically erasable programmable ROM (EEPROM), flash memory, or any other digital media.

IMD 10 may have a housing 15 with a main portion 13, a first projection 17 and a second projection 21 extending from main portion 13. First electrode 16A may be carried by first projection 17 of housing 15. Second electrode 16B may be carried by second projection 21 of housing 15. In other examples of IMD 10, housing 15 may carry one or more additional electrodes, and these electrodes may be disposed on projection 17, projection 21, a location on main portion 13, or some combination thereof. Stimulation circuitry 51 is disposed within main portion 13 of housing 15 and may be configured to generate electrical stimulation deliverable via first 16A and/or second electrode 16B. Processing circuitry 50 may be disposed within main portion 13 of housing 15 and may be configured to control stimulation circuitry 51 to generate the electrical stimulation. Charging circuitry 62 may be disposed within main portion 13 of housing 15 and may be configured to control current from secondary coil 52 to rechargeable power source 68 of IMD 10.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Stimulation circuitry 51 may be selectively coupled to electrodes 16A-16B via switching circuitry 58, as controlled by processing circuitry 50. Stimulation circuitry 51 may deliver electrical stimulation via electrodes 16A-16B in order to provide therapy to a target nerve, such as nerve 8 located in subcutaneous tissue.

Communication circuitry 54 may include any suitable hardware, firmware, software or any combination thereof for communicating with another device, such as external device 12 or another IMD or sensor, such as a pressure sensing device. Under the control of processing circuitry 50, communication circuitry 54 may receive downlink telemetry from, as well as send uplink telemetry to, external device 12 or another device with the aid of an internal or external antenna, e.g., antenna 26. Antenna 26 may be configured to transmit or receive electromagnetic signals for communication. For example, antenna 26 may be configured to transmit to or receive signals from a programmer via inductive coupling, electromagnetic coupling, tissue conductance, NFC, Radio Frequency Identification (RFID), Bluetooth®, Wi-Fi, or other proprietary or non-proprietary wireless telemetry communication schemes. Antenna 26 may be coupled to communication circuitry of IMD 10, which may drive antenna 26 to transmit signals to external device 12 and may transmit signals received from external device 12 to processing circuitry of IMD 10 via communication circuitry. In some examples, communication circuitry 54 may communicate with external device 12. In addition, processing circuitry 50 may communicate with a networked computing device via external device (e.g., external device 12) and a computer network, such as the Medtronic CareLink® Network developed by Medtronic, plc, of Dublin, Ireland.

A clinician or other user may retrieve data from IMD 10 using external device 12, or by using another local or networked computing device configured to communicate with processing circuitry 50 via communication circuitry 54. The clinician may also program parameters of IMD 10 using external device 12 or another local or networked computing device.

Power source 68 is configured to deliver operating power to the components of IMD 10. Power source 68 may include a battery and a power generation circuit to produce the operating power. In some examples, the battery is rechargeable to enable extended operation. In some examples, recharging is accomplished through proximal inductive interaction between an external charger and an inductive charging coil such as secondary coil 52. Charging circuitry 62 then charges the rechargeable battery via the current generated in secondary coil 52. Power source 68 may include any one or more of a plurality of different battery types, such as nickel cadmium batteries and lithium ion batteries. A non-rechargeable battery may be selected to last for months or years depending on usage, while a rechargeable battery may be inductively charged from an external device, e.g., on a daily, weekly, monthly or yearly basis.

FIG. 3 is a conceptual drawing illustrating an example configuration of IMD 10 of the medical device system 2 of FIG. 1, in accordance with one or more techniques described herein. In the example shown in FIG. 3, IMD 10 may include a leadless, subcutaneously implantable stimulating device having housing 15, electrode 16A, and electrode 16B. Housing 15 may further include main portion 13 having first major surface 18, second major surface 20, proximal end 22, and distal end 24. Housing 15 encloses electronic circuitry located inside the IMD 10, and protects the circuitry contained therein from fluids such as body fluids. In some examples, electrical feedthroughs provide electrical connection of electrodes 16A and 16B, and antenna 26, to circuitry within housing 15. In some examples, electrodes 16A and 16B lay at the distal end of projections 17 and 21 respectively.

In the example shown in FIG. 3, IMD 10 is defined by a length L, a width W, and thickness or depth D. In this example, IMD 10 is in the form of an elongated rectangular prism in which length L is significantly greater than width W, and in which width W is greater than depth D. However, other configurations of IMD 10 are contemplated, such as those in which the relative proportions of length L, width W, and depth D vary from those described and shown in FIG. 2. In some examples, the geometry of the IMD 10, such as the width W being greater than the depth D, may be selected to allow IMD 10 to be inserted under the skin of the patient using a minimally invasive procedure and to remain in the desired orientation during insertion. In addition, IMD 10 may include radial asymmetries (e.g., the rectangular shape)

along a longitudinal axis of IMD 10, which may help maintain the device in a desired orientation following implantation.

In some examples, a spacing S between electrode 16A and electrode 16B may range from about 2 centimeters or less, or about 5 mm or less, or any distance in between 5 mm and 2 cm. Overall, IMD 10 may have a length L of about 60 mm or less, or 40 mm or less or any length from 40 mm to 60 mm. In some examples, the width W of major surface 18 may have a width of 8 mm of less, 5 mm or less, or any width in between 8 mm and 5 mm. In some examples, a depth D of IMD 10 may range 5 mm or less, 2 mm or less, or any depth in between 5 mm and 2 mm. In other examples, the depth D of IMD 10 may range from about 2 mm to 5 mm, and may be any single or range of depths from about 2 mm to 9 mm. In any such examples, IMD 10 is sufficiently compact to be implanted within the adipose just under skin 6 or any subcutaneous space of patient 4 located anywhere on patient 4.

IMD 10, according to an example of the present disclosure, may have a geometry and size designed for ease of implant and patient comfort. Examples of IMD 10 described in this disclosure may have a volume of 3 cubic centimeters ($cm^3$) or less, 1.0 $cm^3$ or less, or any volume therebetween. In addition, in the example shown in FIG. 3, proximal end 22 and distal end 24 are rounded to reduce discomfort and irritation to surrounding tissue once implanted under skin 6 of patient 4. In some examples, power may be supplied to IMD 10 through inductive coupling.

In some examples, first major surface 18 of IMD 10 faces outward towards the skin, when IMD 10 is inserted within patient 4, whereas second major surface 20 is facing inward. In some examples, first major surface 18 faces inward towards nerve 8 of patient 4, and second major surface 20 faces outward towards the skin of patient 4.

Electrode 16A and electrode 16B may be used to stimulate nerve 8 with electrical signals (e.g., pulses or continuous waveforms) when IMD 10 is implanted subcutaneously in patient 4. In some examples, one or both of electrodes 16A and 16B also may be used to stimulate nerve 8 of patient 4.

In the example shown in FIG. 3, electrode 16A and electrode 16B are in close proximity to distal end 24 of IMD 10. In this example, electrodes 16A and 16B may be mounted on projections 17 and 21 which may extend from rounded edges 28 or end surface 30 in a three-dimensional curved configuration. As illustrated, electrode 16A is located on projection 17 and is circular and facing toward electrode 16B. However, in other examples not shown here, electrode 16A and electrode 16B both may be configured in other fashions as shown in FIGS. 5A-5J. Any of electrodes 16A-16B may be formed of a biocompatible conductive material. For example, any of electrodes 16A-16B may be formed from any of stainless steel, titanium, platinum, iridium, or alloys thereof. In addition, electrodes of IMD 10 may be coated with a material such as titanium nitride or fractal titanium nitride, although other suitable materials and coatings for such electrodes may be used. Electrodes 16A and 16B may be configured to have any shapes, such as circular, cylindrical, rectangular, triangular, spherical, or other shapes.

In the example shown in FIG. 3, proximal end 22 of IMD 10 includes header assembly 32 having anti-migration projections 34, and suture hole 36.

IMD 10 may include several features for retaining IMD 10 in position once subcutaneously implanted in patient 4. For example, as shown in FIG. 3, housing 15 may include anti-migration projections 34 positioned adjacent integrated antenna 26. Anti-migration projections 34 may include a plurality of bumps or protrusions extending away from first major surface 18 and may help prevent longitudinal movement of IMD 10 after implantation in patient 4. In addition, in the example shown in FIG. 3 header assembly 32 includes suture hole 36, which provides another means of securing IMD 10 to patient 4 to prevent movement following insertion. In some examples, header assembly 32 may include a molded header assembly made from a polymeric or plastic material, which may be integrated or separable from the main portion of IMD 10.

FIG. 4 is a block diagram illustrating an example configuration of components of external device 12, in accordance with one or more techniques of this disclosure. In the example of FIG. 4, external device 12 includes processing circuitry 80, communication circuitry 82, storage device 84, user interface 86, primary coil 87 for recharging IMD 10 and power source 88.

Processing circuitry 80, in one example, may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to alter current operating parameters (e.g., parameter sets that define electrical stimulation delivery) to external device 12. In turn, external device 12 may receive the data from IMD 10 (e.g., remaining power source life) and store the collected data in storage device 84. Additionally, or alternatively, processing circuitry 80 may export instructions to IMD 10 requesting IMD 10 to update electrode combinations for stimulation.

A user, such as a clinician or patient 4, may interact with external device 12 through user interface 86. User interface 86 includes a display (not shown), such as an LCD or LED display or other type of screen, with which processing circuitry 80 may present information related to IMD 10 (e.g., a display of stimulation therapy to nerve 8). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to patient 4, receiving voice commands from patient 4, or both. Storage device 84 may include instructions for operating user interface 86 and for managing power source 88.

Power source 88 is configured to deliver operating power to the components of external device 12. Power source 88 may include a battery and a power generation circuit to produce the operating power. In some examples, the battery is rechargeable to allow extended operation. Recharging may be accomplished by electrically coupling power source 88 to a cradle or plug that is connected to an alternating current (AC) outlet. In addition, power source 88 may recharge IMD 10 through proximal inductive interaction between primary coil 87 and secondary coil 52 (FIG. 2) of IMD 10. In other examples, traditional batteries (e.g., nickel cadmium or lithium ion batteries) may be used. In addition, external device 12 may be directly coupled to an alternating current outlet to operate.

Figure 5I:
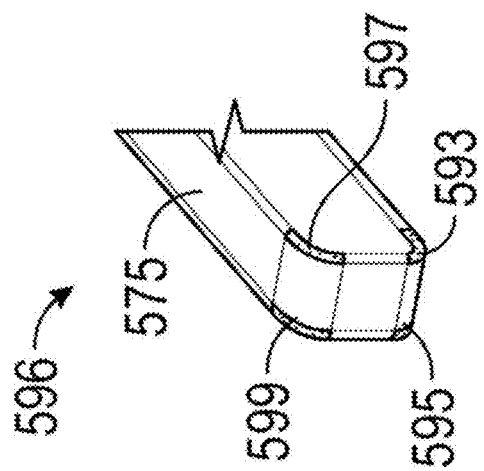

FIGS. 5A, 5B, 5C 5D, 5E, 5F, 5G, 5H, 5I, and 5J are conceptual drawings illustrating example IMDs that may be similar to IMD 10 of FIGS. 1-3, but which may include one or more additional features, in accordance with one or more techniques described herein. FIGS. 5A, 5B, and 5C are conceptual drawings illustrating an IMD 500, 502 and 504 with a main portion 506, 508 and 510 respectively configured with a single projection 512, 520 and 532. FIGS. 5D, 5E, and 5F are conceptual drawings illustrating an IMD 538, 550 and 564 with a main portion 540, 552 and 570 respectively configured with two projections 542 & 544, 554 & 556 and 560 & 562. FIGS. 5G, 5H, 5I, and 5J are conceptual drawings illustrating an IMD 576, 588, 596 and 598 with a main portion 582, 555, 575 and 565 respectively configured with a stunted or no projections.

FIGS. 5A, 5B and 5C show IMDs 500, 502 and 504 with a main portion 506, 508 and 510 respectively. In FIG. 5A, IMD 500 may have a single projection 512. Projection 512 may have an electrode 514 at the distal end of projection 512. Distal end 518 of main portion 506 may house a second electrode 516. When implanted within patient 4, first electrode 514 or second electrode 518 may be placed on, near or adjacent to nerve 8 to provide stimulation.

IMD 502 in FIG. 5B may have a single projection 520. Projection 520 may have an electrode 522 at the distal end of projection 520. Electrode 522 may also work as an attachment mechanism or the attachment mechanism may be located proximal to electrode 522 and be separate from electrode 522. During implantation a clinician may input a stylet (not shown in FIG. 5B) into channel 524 of main portion 508. When a tip of the stylet contacts the back of electrode 522 it causes jaws 526 to extend outward and open (shown as open in FIG. 5B), similar to a concave strip of metal when pressure is applied to the apex of the strip of metal. Pressure on the apex will cause the strip of metal to flatten and open up. When pressure is released off the apex, the metal strip will return to a curved state. The clinician may place projection 520 in a desired location to nerve 8. When projection 520 is placed in the desired location the stylet is removed and jaws 526 close (e.g., return to a natural concave state and release inward toward one another) and pinch adipose and/or tissue between jaws 526, thus securing IMD 502 in place. Further, electrode 528 may reside on distal end 530 and provide a return path for simulation provided through electrode 522.

IMD 504 in FIG. 5C, may also have a single projection 532. Projection 532 may be curved in a fashion which may offer a passive attachment within patient 4. Unlike electrode 522, in FIG. 5B providing an active attachment to tissue or adipose, curved projection 532 may hook onto/into tissue or even around nerve 8 so as to provide a passive attachment (i.e., passive in there is no actuating mechanism for the attachment) for IMD 504. Projection 532 extending from main portion 510 may, when inserted, be curved around nerve 8, thus placing nerve 8 in-between first electrode 534 and second electrode 536. Nerve 8 may then be in the path of electrical current that travels between first 534 and second electrode 536.

IMD 538 in FIG. 5D, with main portion 540 may have a first projection 542 and a second projection 544, which during implantation, may extend around nerve 8. First projection 542 may have first electrode 546 and second projection 544 may have second electrode 548. Nerve 8 may, during implantation, be located in between first electrode 546 and second electrode 548 and thus any stimulation therapy may traverse between the electrodes 546 and 548 and stimulate nerve 8. A dual projection (e.g., first projection 542 and second projection 544) structure may create a channel 541. Channel 541 may have a rounded inner edge to channel 541 that may accept the rounded structure of nerve 8. The dual projection structure of IMD 538 allows for an implanting physician to place an electrode 546 and 548 on both sides of nerve 8. With nerve 8 in between electrodes 546 and 548 very little stimulation energy is needed to provide a stimulation to nerve 8. For example, less than 1 mA may be needed. In another example, channel 541 may be large enough to accept more than one nerve 8 to target stimulation to multiple nerves.

IMD 550 in FIG. 5E may be another example of an IMD 550 with active fixation projections 554 & 556. IMD 550 with main portion 552 may have two projections 554 and 556 extending from main portion 552. During implantation of IMD 550, a stylet may be inserted into channels 558 and 560. The stylet when inserted, causes projections 554 and 556 to extend substantially straight outward. IMD 550 may be inserted subcutaneously placing projections 554 and 556 around nerve 8. The stylet may then be removed which causes projections 554 and 556 to close inward toward one another. Tissue may be pinched between end caps 551 and 553 and nerve 8 may be located between projections 554 and 556. In one example, projections 554 and 556 are semi-flexible or fully flexible and gently surround nerve 8 and hold IMD 550 in place while encapsulation with scar tissue occurs. If IMD 550 would need to be extracted projections 554 and 556 would open up. Electrode 562 is shown on projection 556. A second electrode 561 may be on the underside of projection 554. A stimulation path would travel from or to electrode 562 from or to (depending on polarity) electrode 561 on the underside of projection 554. In another example, electrodes 561 and 562 may also be located on the ends of projections 554 and 556. In this example, a small amount of space may be left in between electrodes 561 and 562 to prevent a possible short and damage to electrodes 561 and 562. In another example, IMD 550 may have electrodes

561, 562 and at end caps 551 and 553. In this example, the implanting physician may have the option to select which electrodes to use for effective stimulation. The implanting physician may elect to use each of the four electrodes 561, 562, 551 and 553.

IMD 564 in FIG. 5F may be an active fixation example similar to IMD 550. Projections 566 and 568 extend from main portion 570. Projections 566 and 568 may be curved inward toward one another and complete a loop 571 which may retain nerve 8 in-between and act to fixate IMD 564 in place and resist movement of IMD 564. Similar to IMD 550, projections 566 and 568 may open and extend outward with the insertion of stylet into channels 567 & 569 within IMD 564. Once IMD 564 is implanted and in place where projections 566 and 568 are located over and under nerve 8, the stylet may be removed. As the stylets are removed projections 566 and 568 begin to close inward toward one another. When the stylet is fully withdrawn projections 566 and 568 are substantially close or touch one another completing loop 571 around nerve 8. A first electrode 572 may be on a mid-portion of projection 566 and a second electrode 574 may be located on a mid-portion of projection 568. Nerve 8 may be in-between electrode 572 and 574 and in the path of an electrical stimulation. Further, the closeness of nerve 8 to electrodes 572 and 574 means very little charge is necessary to provide a simulation to nerve 8.

Figure 5H:
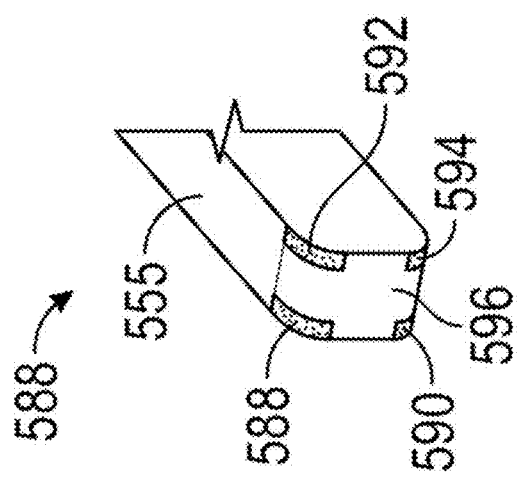
Figure 5J:
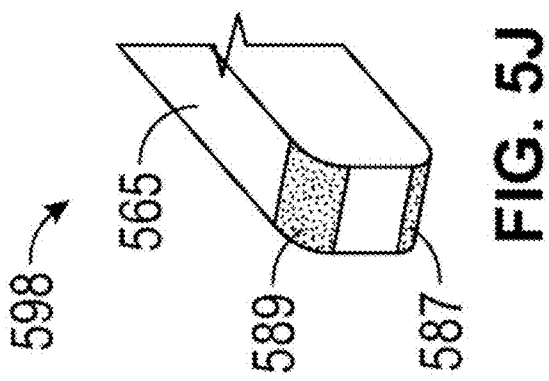
Figure 5G:
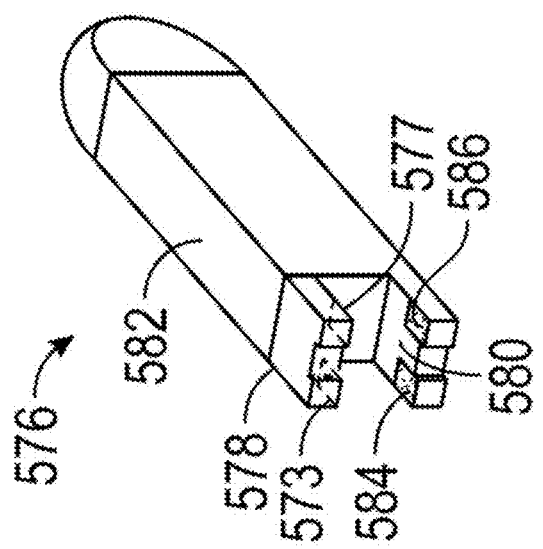

IMD 576 of FIG. 5G may have projections 578 and 580 extending from main portion 582. Each of projections 578 and 580 may have multiple electrodes, such as electrodes 584 and 586 on projection 580 and electrodes 573 and 577 on projection 578. A clinician may have the option of choosing between one to four electrodes for use in stimulation of nerve 8. Further, a clinician may have the option of using a pair of electrodes, such as electrodes 584 and 586 on projection 580 electrodes 573 and 577 on projection 578, electrodes 573 and 584 or electrodes 577 and 586. IMD 576 may offer more opportunities to find a stimulus which assists patient 4 in achieving pain reduction.

IMD 588 of FIG. 5H may have no projections at all and instead may have electrodes 588, 590, 592, and 594 coupled to distal end 596 of main portion 555. IMD distal end 596 may be placed proximal to nerve 8 and a clinician may pick and choose which electrodes and how many of electrodes 588, 590, 592 and 594 to use. Electrodes 588, 590, 592, and 594 may have a curved orientation. The curvature may allow for an implanting physician to move and rotate main portion 555 while keeping one or more of electrodes 588, 590, 592, or 594 in position to apply stimulation. For example, each of electrodes 588, 590, 592, and 594 may have a 90-degree rotation capacity (i.e., main portion 555 may be rotated 90 degrees and still maintain contact with a target nerve 8 for stimulation). This may allow for main portion 555 to have better positioning ability for an implanting physician when working with nerves in a shallow location.

IMD 596 of FIG. 5I and IMD 598 of FIG. 5J may have a similar structure. IMD 596 of FIG. 5I may have four electrodes 599, 597, 595 and 593 on distal end 591 of main portion 575. Electrodes 599, 597, 595 and 593 may be rounded on distal end 591 to reduce discomfort and irritation to surrounding tissue once implanted under skin 6 of patient 4. IMD 598 of FIG. 5J may have two electrodes 589 and 587 at a distal end of main portion 565 with a larger contact surface area and a rounded surface to reduce discomfort and irritation to surrounding tissue.

Figure 6A:
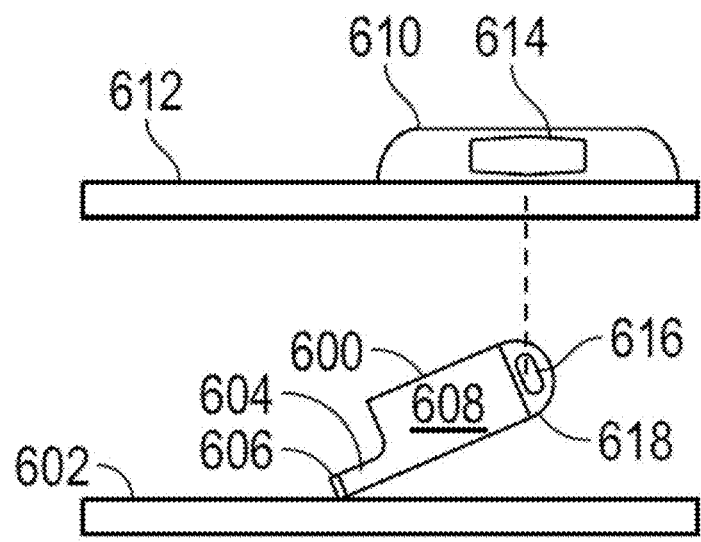
FIGS. 6A and 6B are conceptual drawings illustrating an example IMD implanted subcutaneously in accordance with one or more techniques described herein.
Figure 6B:
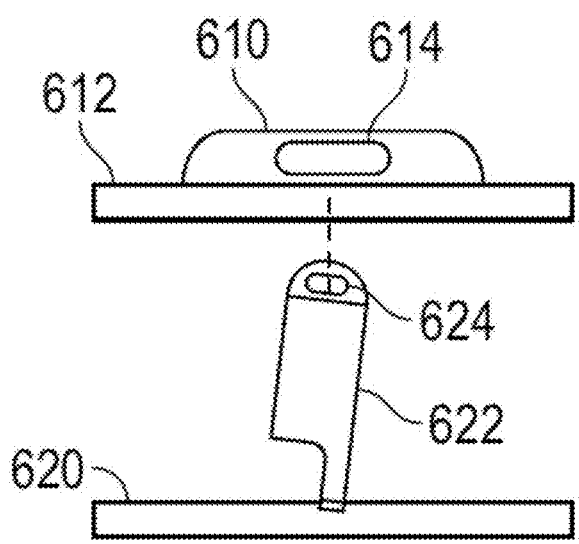

FIGS. 6A and 6B are conceptual drawings illustrating an example IMD implanted subcutaneously in accordance with one or more techniques described herein. IMD 600 may be similar to any of the IMDs described herein. In FIG. 6A, IMD 600 may be implanted near a shallow nerve 602 and thus IMD 600 may be placed in a horizontal manner as shown in FIG. 6A or even substantially parallel to nerve 602 to the extent both of projections 604 are on both sides of nerve 602. Projection 604 with electrode 606 extend away from main portion 608 toward nerve 602. Electrode 606 may be in contact, near or adjacent to nerve 602 to provide stimulation.

External device 610 may be on the surface of skin 612. External device 610 may communicate with or charge IMD 600 through inductive coupling primary coil 614 with secondary coil 616. During implantation, a clinician may tilt IMD 600 at an angle so proximal end 618 of IMD 600 may be closer to skin 612 to allow for communication. Resonant inductive coupling may achieve high efficiency at ranges of 4 to 10 times the coil diameter. This is called "mid-range" transfer, in contrast to the "short range" of non-resonant inductive transfer, which may achieve similar efficiencies only when the coils are adjacent. Thus, since secondary coil 616 may have a shorter diameter, the range of communication transfer between primary coil 614 and secondary coil 616 may be a few millimeters to a few centimeters. Thus, proximal end 618 may be pointed toward skin 612 to shorten the distance between primary coil 614 and secondary coil 616.

In the example of FIG. 6B, nerve 620 may be located deeper under skin 612. Therefore, a clinician may want to extend IMD 622 in a more vertical arrangement to place secondary coil 624 closer to skin 612 and primary coil 614. Power transfer of inductive coupling occurs by creating an alternating magnetic field on primary coil 614. The magnetic field is then converted into an electrical current in secondary coil 624. The generated electrical current, which is filtered by the charging circuitry and sent to the power source, depends on the amount of magnetic flux generated by primary coil 614 and how much of the magnetic flux secondary coil 624 is able to capture. The distance, size and positioning of secondary coil 624 relative to the primary coil 87 determines how much magnetic flux secondary coil 624 captures. Alignment of primary coil 614 with secondary coil 624 is determinative of the power transfer. Thus, if during implantation secondary coil 624 is not aligned with primary coil 614, proper transfer may not occur. This may be very difficult in situations where nerve 8 is deeper under skin 6 and IMD 622 requires being placed in a vertical orientation or if IMD 622 rotates after implantation.

Figure 7:
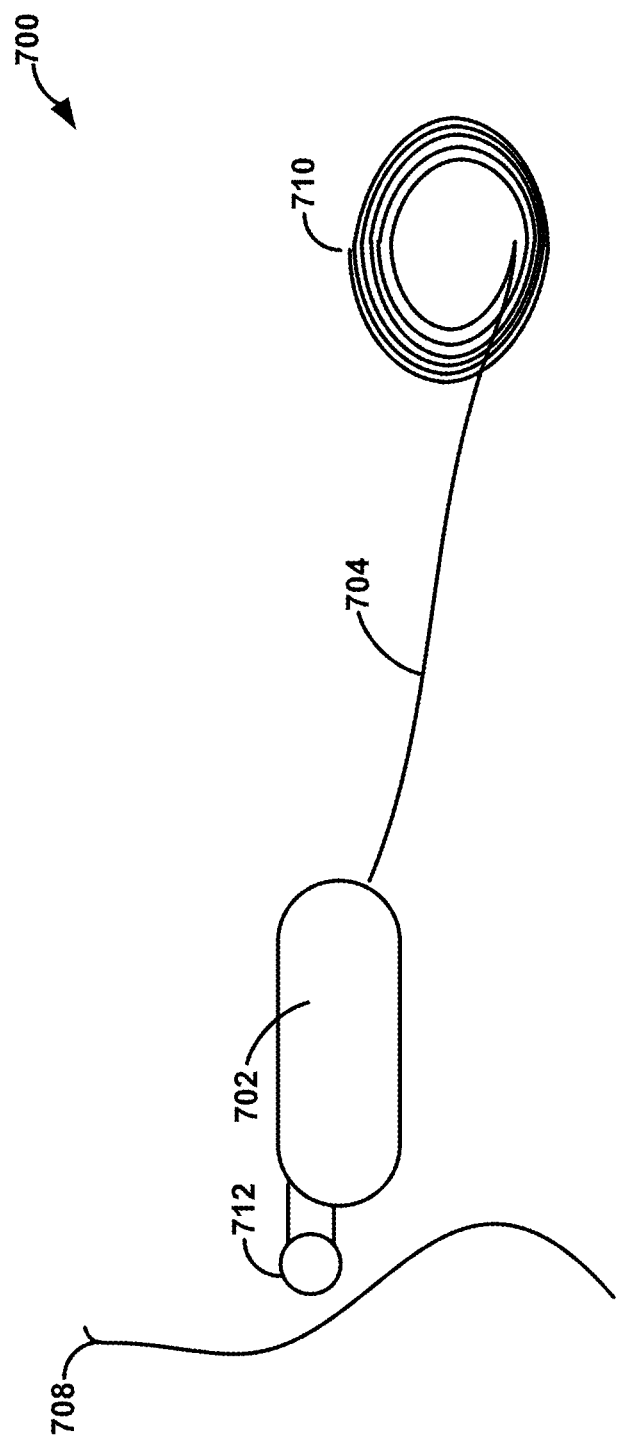
FIG. 7 is a conceptual drawing illustrating a coil shaped recharging IMD in accordance with one or more techniques described herein.

FIG. 1 is a conceptual drawing illustrating a recharging IMD 700 in accordance with one or more techniques described herein. FIG. 7 is a front profile view of a recharging IMD 700. Recharging IMD 700 may simplify an implantation method for the IMDs of FIGS. 1-3 and/or 5A, 5B, 5C, 5D, 5E, 5F, 5G, 5H, 5I, or 5J. Recharging IMD 700 may have housing 702 which may be similar to the housings of FIGS. 1-3 and/or 5A, 5B, 5C, 5D, 5E, 5F, 5G, 5H, 5I or 5J. An electrical connection 704 couples housing 702 to appendage 710 (e.g., a secondary coil). Appendage 710 may be comprised of a coiled conductor. Appendage 710 may be similar to secondary coil 52 in that it may be able to receive inductive energy from primary coil 87. Electrical connection 704 and appendage 710 may be constructed of an electrically conductive material, such as a metal or metal alloy. An electrically insulative material (e.g., a polymer or other non-conductive material) may cover electrical connection 704 and appendage 710.

Target nerve 708 may be located at varying depths of subcutaneous tissue. In situations where housing 702 may need to be implanted deeply to place electrode 712 near to or in contact with nerve 708, then it may be desirable to utilize recharging IMD 700 to not only recharge an IMD power source, but also to provide RF communications (e.g., act as an antenna), provide a way of locating IMD 700 and be used as a tether to remove IMD 700. Recharging IMD 700 may allow for implantation in most any fashion with little worry about keeping secondary coil 52 close to the surface of skin 6. After the implantation of housing 702, appendage 710 may be left close to skin 6, thus the orientation of housing 702 may not influence recharge of IMD 700.

Unlike the arrangement in FIGS. 6A and 6B, with recharging IMD 700 the orientation of the housing 702 does not affect inductive coupling. The clinician can focus on implanting electrode 712 in a position relative to nerve 708 to provide proper stimulation. Once IMD 700 is implanted, electrical connection 704 and appendage 710 can be extended toward the surface of the skin. Appendage 710 can then be laid parallel with the skin surface which will enable appropriate positioning of the secondary coil to inductively couple with the primary coil of external device 12.

Recharging IMD 700 may be coupled to housing 702 allowing housing 702 to be inserted near nerve 708 and implanted as deep as necessary without concern about the secondary coil and the primary coil being able to inductively couple. Instead, recharging IMD 700 may couple directly to the charging circuitry within housing 702. IMD 700 may be implanted in a single step. Appendage 710 may inductively couple with the primary coil of external device 12 and convert the magnetic flux into current and route the current through electrical connector 704 to housing 702 to recharge the IMD power source. In another example, appendage 710 may have a helix shape, which may provide for more flexibility when placing appendage 710 near the skin (e.g., appendage 710 may not need to be parallel with the skin surface).

Electrical connector 704 may be flexible and electrically connect appendage 710 to housing 702. Appendage 710 may also enable RF coupling to communicate between communication circuitry within housing 702 and external device 12 and the ability to locate housing 702 at varying anatomical depths.

Figure 8:
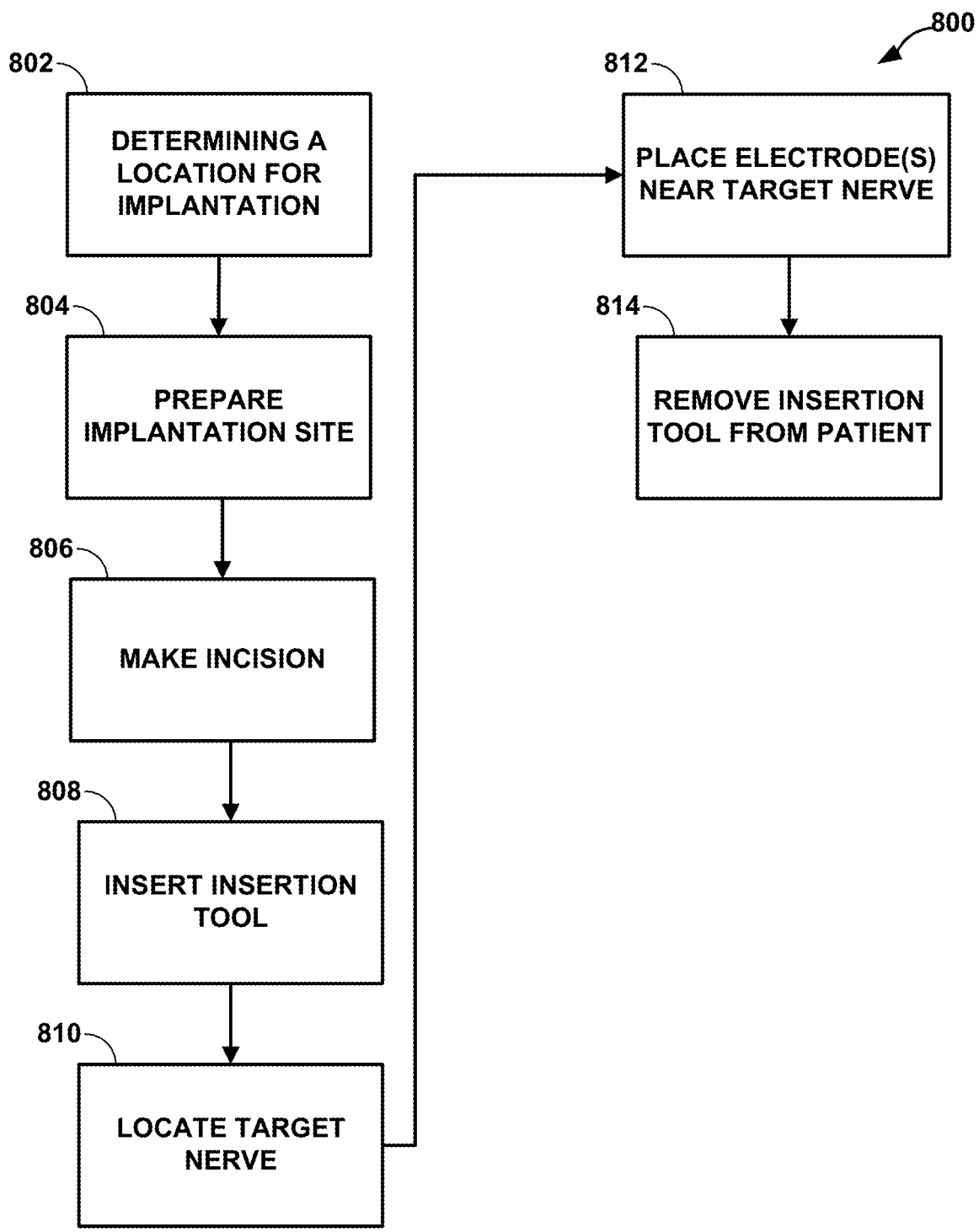
FIG. 8 is a flow diagram illustrating an example operation for implanting an IMD near a nerve, in accordance with one or more techniques of this disclosure.

FIG. 8 is a flow diagram illustrating an example operation 800 for implanting an IMD near a target nerve, in accordance with one or more techniques of this disclosure. IMD 10 will be used for the example of FIG. 8, but any IMDs described herein may be used in the technique of FIG. 8. In the example of FIG. 8, a clinician, physician and/or surgeon determines a location for implantation of IMD 10 (802). During implantation the implantation site is prepared through cleaning with antiseptic (804). The implanting physician may make an incision under the skin and into the subcutaneous tissue (806). The implanting physician inserts an insertion tool with the IMD into the incision (808). The implanting physician locates the target nerve (810) and inserts the electrodes of the IMD adjacent to the target nerve (812). In some examples, the clinician may generate test stimulation from IMD 10 in order to ensure the electrodes are disposed at a correct location with respect to the target nerve. The insertion tool may then be removed from the patient when the IMD is fully implanted within the patient (814).

Figure 9:
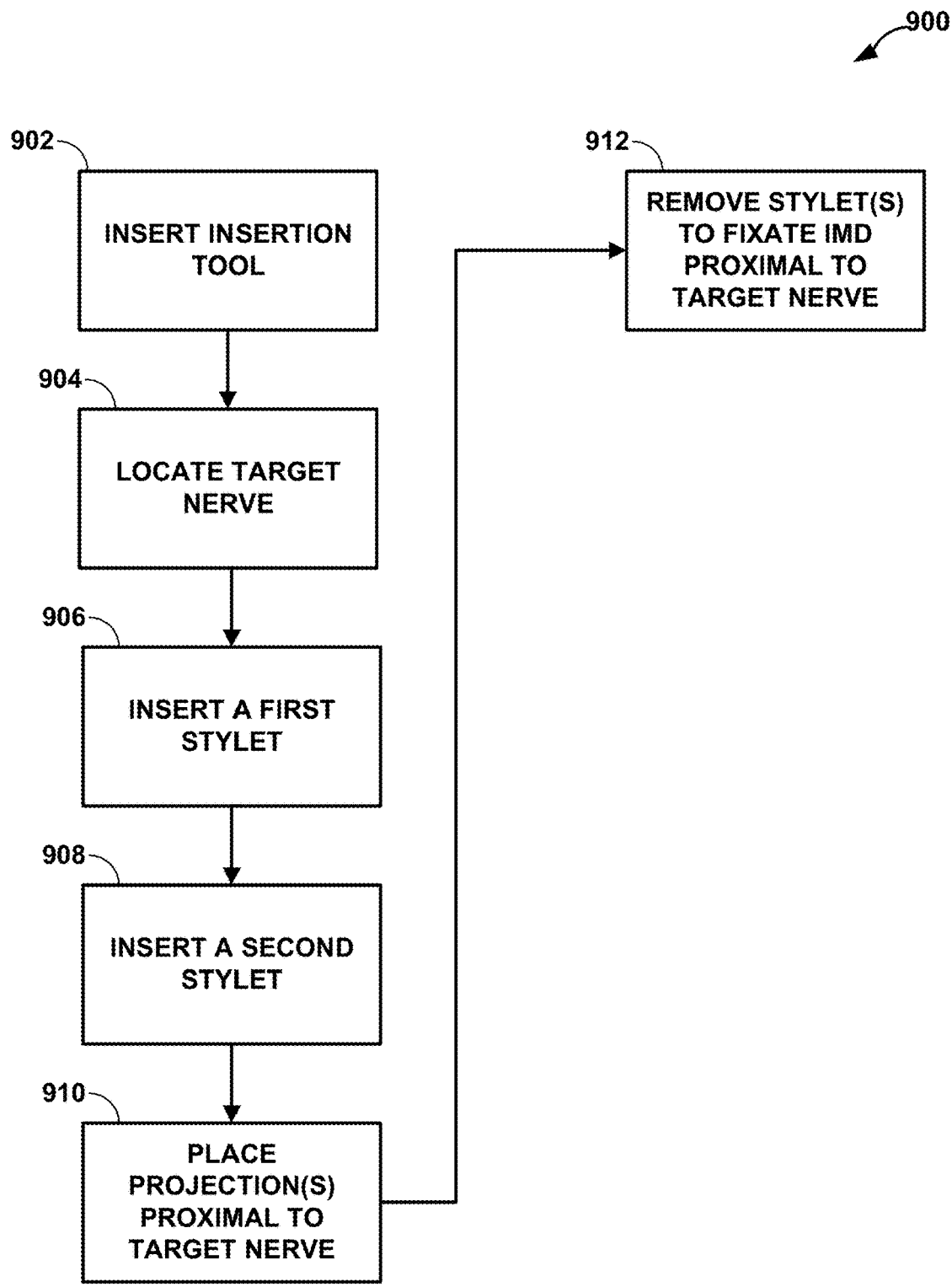
FIG. 9 is a flow diagram illustrating an example operation for implanting an IMD with a curved projection near a nerve, in accordance with one or more techniques of this disclosure.

FIG. 9 is a flow diagram illustrating an example operation 900 for implanting an IMD with a curved projection near a nerve, in accordance with one or more techniques of this disclosure. In the example of FIG. 9, an implantation physician inserts an insertion tool with the IMD, into the incision (902). The implanting physician locates a target nerve (904). The implanting physician inserts a single stylet (e.g., for an IMD similar IMD 502) (906). The implanting physician inserts a second stylet (e.g., for an IMD similar to IMD 550 and/or 564) (908). In another example, the implanting physician may insert the stylets into the IMDs prior to placement of the IMDs into the insertion tool. In another example, the implanting physician the stylets may be placed into the IMD before the insertion tool is placed within the incision. The placement of the stylets may be a matter of preference for the implantation physician. As discussed briefly above, when the stylets are inserted into channels within the IMDs, the projections straighten from a curved state into extending substantially straight. The stylets may be inserted during implantation or when the IMD is proximal to a targeted nerve. When the IMD is still within the insertion tool, there is no resistance to the projections straightening out. When the IMD is outside of the insertion tool proximal to the target nerve, there may be a small amount of resistance to the projections straightening out as tissue will push against the projections; however, the resistance should not be great.

When the projection(s) are substantially straight the implanting clinician places the projection(s) proximal to the target nerve by advancing the IMD forward (910). The implanting physician removes the stylet(s), which will cause the projection(s) to return to their normally curved state. The target nerve is located between a pair of electrodes on the IMD, and the curved projection(s) may act as a fixation mechanism to keep the IMD in place for stimulation and prevent IMD movement (912). In another example, additional examples may be used such as suture hole 36 and/or anti-migration projections 34.

Figure 10:
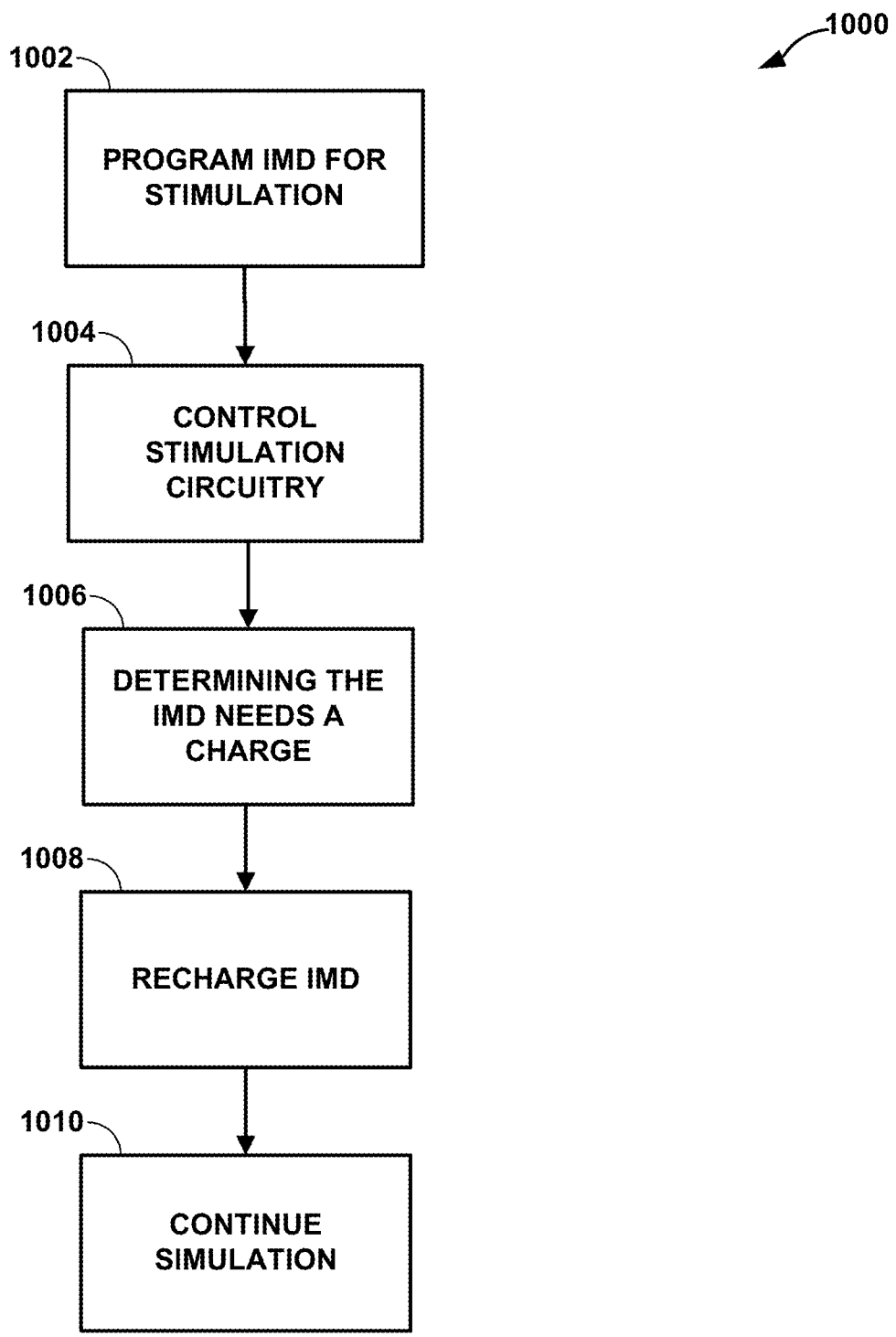
FIG. 10 is a flow diagram illustrating an example operation for simulation of an IMD, in accordance with one or more techniques of this disclosure.
Figure 11:
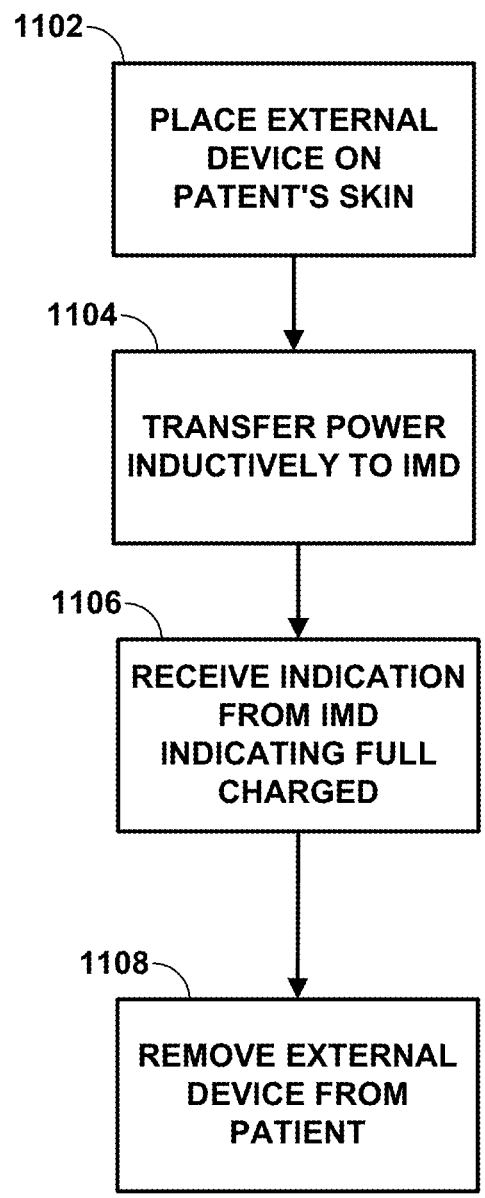
FIG. 11 is a flow diagram illustrating an example operation for charging an IMD, in accordance with one or more techniques of this disclosure.

FIG. 10 is a flow diagram illustrating an example operation for simulation of an IMD, such as IMD 10, in accordance with one or more techniques of this disclosure. An implanting physician or clinician or physician may program the IMD to provide stimulation after implantation with external device 12 (1002). In another example, the IMD may be preprogrammed for stimulation before implantation. After-implantation programming of the IMD may provide effective therapy for the patient. The IMD begins to control stimulation circuitry 51 to delivering stimulation therapy (1004). Processing circuitry 50 may determine the IMD needs to have power source 68 charged (1006). The IMD may communicate to external device 12 the IMD needs a charge. A user, the patient, clinician or a physician, places external device 12 over skin 6 and begin a charging process (1008) (FIG. 11). After a charging session, discussed in FIG. 11, the IMD may continue with a stimulation therapy administration (1010).

FIG. 11 is a flow diagram illustrating another example operation for charging an IMD, in accordance with one or more techniques of this disclosure. In the event an IMD of FIG. 1, 2, 3, 5A, 5B, 5C, 5D, 5E, 5F, 5G, 5H, 5I or 5J needed to have their power source recharged, the patient, a clinician or a physician uses external device 12 to recharge the IMD power source. A user places external device 12 on patient's skin 6 in the general location of the IMD, such as IMD 10 (1102). In one example, a user interface of external device 12 is used to show an alignment with the secondary coil of IMD 10 to enable a user to align the primary coil of external device 12 with the secondary coil. This detection is performed through RF coupling and detection of signal strength coming from IMD 10. Once external device 12 is determined to be properly aligned with the secondary coil of the IMD or a coil 710 of the coil shaped recharging system 700 of FIG. 7, external device 12 transfers power inductively from the primary coil to the secondary coil or the coil 710 (1104).

IMD 10 communicates with external device 12 such that external device 12 receives an indication the power source onboard IMD 10 is fully charged (1106). In other examples, external device 12 may receive periodic or continuous indications from IMD 10 regarding the charge level of the rechargeable power supply of IMD 10. Once IMD 10 is recharged, external device 12 discontinues power transfer and the user removes external device 12 from the patient (1108)

The following is a non-limiting list of examples that are in accordance with one or more techniques of this disclosure.

Example 1A. An implantable medical device comprising: a housing comprising a main portion and projection extending from the main portion; an electrode carried by the projection of the housing; stimulation circuitry disposed within the main portion of the housing, wherein the stimulation circuitry is configured to generate electrical stimulation deliverable via the electrode; and processing circuitry disposed within the main portion of the housing, wherein the processing circuitry is configured to control the stimulation circuitry to generate the electrical stimulation.

Example 2A. The implantable medical device of example 1A, wherein the projection is a first projection, the electrode is a first electrode, and the housing comprises a second projection extending from the main portion, wherein the implantable medical device further comprises: a second electrode carried by the second projection of the housing, wherein the stimulation circuitry is configured to generate electrical stimulation deliverable via the first electrode and the second electrode.

Example 3A. The implantable medical device of example 2A, wherein the first projection and the second projection extend from the main portion in approximately a same direction, the first projection and the second projection configured to be disposed on opposing sides of a nerve.

Example 4A. The implantable medical device of example 2A, wherein both the first projection and the second projection extend straight out from the main portion of the housing.

Example 5A. The implantable medical device of example 2A, wherein: the first projection comprises a first curved distal portion curved towards the second projection; the second projection comprises a second curved distal portion curved towards the first projection; the first electrode is disposed proximal from a tip of the first projection; and the second electrode is disposed proximal from a tip of the second projection.

Example 6A. The implantable medical device of example 5A, wherein: the first projection and the second projection are pre-curved; both the first projection and the second projection define respective channels configured to receive a stylet, the first projection and the second projection configured to straighten in response to the stylet being inserted into the respective channels to implant the first and second projections around a target nerve; and removal of the stylet enables the first projection and the second projection to revert to the pre-curved form of the first projection and the second projection to capture the target nerve within the first projection and the second projection.

Example 7A. The implantable medical device of example 1A, wherein the electrode is a first electrode, and wherein the implantable medical device further comprises a second electrode carried by the main portion of the housing.

Example 8A. The implantable medical device of any of examples 1A-7A, further comprising: a secondary coil configured to receive power from an external primary coil; a rechargeable power source; and charging circuitry configured to control charging of the rechargeable power source using current generated from the secondary coil.

Example 9A. The implantable medical device of example 8A, wherein the secondary coil is disposed within the main portion of the housing.

Example 10A. The implantable medical device of example 8A, further comprising an appendage extending from the main portion of the housing, wherein the appendage comprises the secondary coil.

Example 11A. The implantable medical device of any of examples 1A-10A, further comprising one or more fixation structures extending from the main portion of the housing, each fixation structure of the one or more fixation structures configured to retain the implantable medical device at a target location.

Example 12A. The implantable medical device of any of examples 1A-11A, wherein the housing comprises a volume from approximately 1 cubic centimeter (cc) to approximately 2 cc.

Example 1B. A method comprising: controlling, by processing circuitry disposed within a housing of an implantable medical device, stimulation circuitry of the implantable medical device to generate electrical stimulation, wherein: the housing comprises a main portion and a projection extending from the main portion, the projection of the housing carries an electrode, and the stimulation circuitry and the processing circuitry are disposed within the main portion of the housing; and delivering, via at least the electrode carried by the projection, the electrical stimulation to a target nerve.

Example 2B. The method of example 1B, wherein the projection is a first projection, the electrode is a first electrode, and the housing comprises a second projection extending from the main portion and carrying a second electrode, and wherein delivering the electrical stimulation to the target nerve further comprises delivering, via the first electrode and the second electrode, the electrical stimulation to the target nerve.

Example 3B. The method of example 2B, wherein the first projection and the second projection extend from the main portion in approximately a same direction.

Example 4B. The method of example 3B, wherein both the first projection and the second projection extend straight out from the main portion of the housing.

Example 5B. The method of example 2B, wherein: the first projection comprises a first curved distal portion curved towards the second projection; the second projection comprises a second curved distal portion curved towards the first projection; the first electrode is disposed proximal from a tip of the first projection; and the second electrode is disposed proximal from a tip of the second projection.

Example 6B. The method of example 1B, wherein the projection is a first projection, the electrode is a first electrode, and the housing comprises a second electrode on the main portion, and wherein delivering the electrical stimulation to the target nerve further comprises delivering, via the first electrode and the second electrode, the electrical stimulation to the target nerve.

Example 7B. The method of any of examples 1B-6B, further comprising: charging a rechargeable power source with charging circuitry configured to control charging of the rechargeable power source using current generated from a secondary coil configured to receive power from an external primary coil.

Example 1C. An implantable medical device comprising: a housing comprising: a main portion; a first projection extending from the main portion; and a second projection extending from the main portion, wherein the first projection and the second projection are configured to be disposed on opposing sides of a nerve; a first electrode carried by the first projection of the housing; a second electrode carried by the second projection of the housing; stimulation circuitry disposed within the main portion of the housing, wherein the stimulation circuitry is configured to generate electrical stimulation deliverable via the first or second electrode; processing circuitry disposed within the main portion of the housing, wherein the processing circuitry is configured to control the stimulation circuitry to generate the electrical stimulation; and charging circuitry disposed within the main portion of the housing, wherein the charging circuitry is configured to control current from a secondary coil to a rechargeable power source of the implantable medical device.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. Also, the techniques may be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. An implantable medical device comprising:
   an implantable housing configured to be fully implanted within a patient, wherein the implantable housing comprises a main portion, a first projection, and a second projection, the first projection and the second projection extending from the main portion in approximately a same direction, wherein a cross-sectional dimension of the main portion is larger than a cross-sectional dimension of the first projection and the second projection, and wherein a length of the first projection and the second projection is shorter than a length of the main portion;
   a first electrode carried by the first projection of the housing;
   a second electrode carried by the second projection of the housing;
   stimulation circuitry disposed within the main portion of the housing, wherein the stimulation circuitry is configured to generate electrical stimulation deliverable via at least one of the first electrode and the second electrode; and
   processing circuitry disposed within the main portion of the housing, wherein the processing circuitry is configured to control the stimulation circuitry to generate the electrical stimulation.

2. The implantable medical device of claim 1, wherein the first projection and the second projection are configured to be disposed on opposing sides of a nerve, and wherein the first electrode and the second electrode are configured to deliver the electrical stimulation to the nerve.

3. The implantable medical device of claim 1, wherein both the first projection and the second projection extend straight out from the main portion of the housing.

4. The implantable medical device of claim 1, wherein:
   the first projection comprises a first curved distal portion curved towards the second projection;
   the second projection comprises a second curved distal portion curved towards the first projection;
   the first electrode is disposed proximal from a tip of the first projection; and
   the second electrode is disposed proximal from a tip of the second projection.

5. The implantable medical device of claim 4, wherein:
   the first projection and the second projection are pre-curved;
   both the first projection and the second projection define respective channels configured to receive a stylet, the first projection and the second projection configured to straighten in response to the stylet being inserted into the respective channels to implant the first and second projections around a target nerve; and
   removal of the stylet enables the first projection and the second projection to revert to the pre-curved form of the first projection and the second projection to capture the target nerve within the first projection and the second projection.

6. The implantable medical device of claim 1, wherein the implantable medical device further comprises a third electrode carried by the main portion of the housing.

7. The implantable medical device of claim 1, further comprising:
   a secondary coil configured to receive power from an external primary coil;
   a rechargeable power source; and
   charging circuitry configured to control charging of the rechargeable power source using current generated from the secondary coil.

8. The implantable medical device of claim 7, wherein the secondary coil is disposed within the main portion of the housing.

9. The implantable medical device of claim 7, further comprising an appendage extending from the main portion of the housing, wherein the appendage comprises the secondary coil.

10. The implantable medical device of claim 1, further comprising one or more fixation structures extending from the main portion of the housing, each fixation structure of the one or more fixation structures configured to retain the implantable medical device at a target location.

11. The implantable medical device of claim 1, wherein the a volume of the housing is between approximately 1 cubic centimeter (cc) to approximately 2 cc.

12. The implantable medical device of claim 1, wherein the implantable housing, including the main portion and the projection, is configured to be fully inserted into the patient in a single step.

13. The implantable medical device of claim 1, wherein the implantable housing has a length less than 40 mm, a width less than 8 mm, and a depth less than 5 mm.

14. The implantable medical device of claim 1, wherein the stimulation circuitry is configured to generate electrical stimulation that reduces pain for the patient.

15. A method comprising:
controlling, by processing circuitry disposed within an implantable housing of an implantable medical device, stimulation circuitry of the implantable medical device to generate electrical stimulation, wherein:
the implantable housing is configured to be fully implanted within a patient, the implantable housing comprising a main portion, a first projection, and a second projection, the first projection and the second projection extending from the main portion in approximately a same direction, wherein a cross-sectional dimension of the main portion is larger than a cross-sectional dimension of the first projection and the second projection, and wherein a length of the first projection and the second projection is shorter than a length of the main portion,
the first projection of the housing carries a first electrode,
the second projection of the housing carries a second electrode, and
the stimulation circuitry and the processing circuitry are disposed within the main portion of the housing; and
delivering, via at least the first electrode carried by the first projection or the second electrode carried by the second projection of the implantable housing fully implanted within the patient, the electrical stimulation to a target nerve.

16. The method of claim 15, wherein delivering the electrical stimulation to the target nerve further comprises delivering, via the first electrode and the second electrode configured to be disposed on opposing sides of the target nerve, the electrical stimulation to the target nerve.

17. The method of claim 16, wherein both the first projection and the second projection extend straight out from the main portion of the housing.

18. The method of claim 15, wherein:
the first projection comprises a first curved distal portion curved towards the second projection;
the second projection comprises a second curved distal portion curved towards the first projection;
the first electrode is disposed proximal from a tip of the first projection; and
the second electrode is disposed proximal from a tip of the second projection.

19. The method of claim 15, wherein the housing comprises a third electrode on the main portion, and wherein delivering the electrical stimulation to the target nerve further comprises delivering, via the third electrode, the electrical stimulation to the target nerve.

20. The method of claim 15, further comprising:
charging a rechargeable power source with charging circuitry configured to control charging of the rechargeable power source using current generated from a secondary coil configured to receive power from an external primary coil.

21. An implantable medical device comprising:
an implantable housing configured to be fully implanted within a patient, wherein the implantable housing comprises:
a main portion;
a first projection extending from the main portion; and
a second projection extending from the main portion, wherein the first projection and the second projection extend from the main portion in approximately a same direction and are configured to be disposed on opposing sides of a nerve, wherein a cross-sectional dimension of the main portion is larger than both of a cross-sectional dimension of the first projection and a cross-sectional dimension of the second projection, and wherein a length of the main portion is longer than both of a length of the first projection and a length of the second projection;
a first electrode carried by the first projection of the housing;
a second electrode carried by the second projection of the housing;
stimulation circuitry disposed within the main portion of the housing, wherein the stimulation circuitry is configured to generate electrical stimulation deliverable via at least the first electrode or the second electrode;
processing circuitry disposed within the main portion of the housing, wherein the processing circuitry is configured to control the stimulation circuitry to generate the electrical stimulation; and
charging circuitry disposed within the main portion of the housing, wherein the charging circuitry is configured to control current from a secondary coil to a rechargeable power source of the implantable medical device.

* * * * *